(12) United States Patent
Yamamoto

(10) Patent No.: US 9,677,901 B2
(45) Date of Patent: Jun. 13, 2017

(54) SYSTEM AND METHOD FOR PROVIDING NAVIGATION INSTRUCTIONS AT OPTIMAL TIMES

(71) Applicant: Toyota Motor Engineering & Manufacturing North America, Inc., Erlanger, KY (US)

(72) Inventor: Kenichi Yamamoto, San Jose, CA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 50 days.

(21) Appl. No.: 14/643,994

(22) Filed: Mar. 10, 2015

(65) Prior Publication Data

US 2016/0265917 A1   Sep. 15, 2016

(51) Int. Cl.
| | | |
|---|---|---|
| *G01C 21/14* | (2006.01) | |
| *G01C 21/36* | (2006.01) | |
| *A61F 9/08* | (2006.01) | |
| *A61H 3/06* | (2006.01) | |
| *G01C 21/16* | (2006.01) | |

(Continued)

(52) U.S. Cl.
CPC ............ *G01C 21/3655* (2013.01); *A61F 9/08* (2013.01); *A61H 3/06* (2013.01); *G01C 21/14* (2013.01); *G01C 21/16* (2013.01); *G01C 21/165* (2013.01); *G02B 27/017* (2013.01); *G02C 11/10* (2013.01)

(58) Field of Classification Search
CPC .... G01C 21/14; G01C 21/206; G01C 21/165; G01C 21/16; G01C 21/3655; A61H 3/06; G06F 1/163; A61F 9/08; G02C 11/10; G02C 5/001; G02C 5/14; G02B 2027/0178; G02B 27/017
See application file for complete search history.

(56) References Cited

U.S. PATENT DOCUMENTS

| | | |
|---|---|---|
| 4,520,501 A | 5/1985 | DuBrucq |
| 4,586,827 A | 5/1986 | Hirsch et al. |
| 5,047,952 A | 9/1991 | Kramer |

(Continued)

FOREIGN PATENT DOCUMENTS

| | | |
|---|---|---|
| CN | 201260746 | 6/2009 |
| CN | 101527093 | 9/2009 |

(Continued)

OTHER PUBLICATIONS

The Nex Band; http://www.mightycast.com/#faq; May 19, 2015; 4 pages.

(Continued)

*Primary Examiner* — Jason Holloway
(74) *Attorney, Agent, or Firm* — Snell & Wilmer LLP

(57) ABSTRACT

A wearable smart device for alerting a user of an upcoming turn or object. The wearable smart device includes a camera configured to detect image data. The wearable smart device also includes a processor coupled to the camera and configured to determine a current speed of the wearable smart device based on the image data. The processor is also configured to determine when a navigation instruction is to be output based on the current speed. The wearable smart device also includes an output unit coupled to the processor and configured to output the navigation instruction.

11 Claims, 7 Drawing Sheets

(51) Int. Cl.
  *G02C 11/00*  (2006.01)
  *G02B 27/01*  (2006.01)

(56) References Cited

U.S. PATENT DOCUMENTS

| | | | |
|---|---|---|---|
| 5,097,856 A | 3/1992 | Chi-Sheng | |
| 5,129,716 A | 7/1992 | Holakovsky et al. | |
| 5,265,272 A | 11/1993 | Kurcbart | |
| 5,463,428 A | 10/1995 | Lipton et al. | |
| 5,508,699 A | 4/1996 | Silverman | |
| 5,539,665 A | 7/1996 | Lamming et al. | |
| 5,543,802 A | 8/1996 | Villevieille | |
| 5,544,050 A | 8/1996 | Abe | |
| 5,568,127 A | 10/1996 | Bang | |
| 5,636,038 A | 6/1997 | Lynt | |
| 5,659,764 A | 8/1997 | Sakiyama | |
| 5,701,356 A | 12/1997 | Stanford et al. | |
| 5,733,127 A | 3/1998 | Mecum | |
| 5,807,111 A | 9/1998 | Schrader | |
| 5,872,744 A | 2/1999 | Taylor | |
| 5,953,693 A | 9/1999 | Sakiyama | |
| 5,956,630 A | 9/1999 | Mackey | |
| 5,982,286 A | 11/1999 | Vanmoor | |
| 6,009,577 A | 1/2000 | Day | |
| 6,055,048 A | 4/2000 | Langevin et al. | |
| 6,067,112 A | 5/2000 | Wellner et al. | |
| 6,199,010 B1 | 3/2001 | Richton | |
| 6,229,901 B1 | 5/2001 | Mickelson et al. | |
| 6,230,135 B1 | 5/2001 | Ramsay | |
| 6,230,349 B1 | 5/2001 | Silver et al. | |
| 6,285,757 B1 | 9/2001 | Carroll et al. | |
| 6,307,526 B1 | 10/2001 | Mann | |
| 6,323,807 B1 | 11/2001 | Golding et al. | |
| 6,349,001 B1 | 2/2002 | Spitzer | |
| 6,466,232 B1 | 10/2002 | Newell | |
| 6,542,623 B1 | 4/2003 | Kahn | |
| 6,580,999 B2 | 6/2003 | Maruyama et al. | |
| 6,594,370 B1 | 7/2003 | Anderson | |
| 6,603,863 B1 | 8/2003 | Nagayoshi | |
| 6,619,836 B1 | 9/2003 | Silvant et al. | |
| 6,701,296 B1 | 3/2004 | Kramer | |
| 6,774,788 B1 | 8/2004 | Balfe | |
| 6,825,875 B1 | 11/2004 | Strub et al. | |
| 6,826,477 B2 | 11/2004 | Ladetto et al. | |
| 6,834,373 B2 | 12/2004 | Dieberger | |
| 6,839,667 B2 | 1/2005 | Reich | |
| 6,857,775 B1 | 2/2005 | Wilson | |
| 6,920,229 B2 | 7/2005 | Boesen | |
| D513,997 S | 1/2006 | Wilson | |
| 7,027,874 B1 | 4/2006 | Sawan et al. | |
| D522,300 S | 6/2006 | Roberts | |
| 7,069,215 B1 | 6/2006 | Bangalore | |
| 7,106,220 B2 | 9/2006 | Gourgey et al. | |
| 7,228,275 B1 | 6/2007 | Endo | |
| 7,299,034 B2 | 11/2007 | Kates | |
| 7,308,314 B2 | 12/2007 | Havey et al. | |
| 7,336,226 B2 | 2/2008 | Jung et al. | |
| 7,356,473 B2 | 4/2008 | Kates | |
| 7,413,554 B2 | 8/2008 | Kobayashi et al. | |
| 7,417,592 B1 | 8/2008 | Hsiao et al. | |
| 7,428,429 B2 | 9/2008 | Gantz et al. | |
| 7,463,188 B1 | 12/2008 | McBurney | |
| 7,496,445 B2 | 2/2009 | Mohsini | |
| 7,501,958 B2 | 3/2009 | Saltzstein et al. | |
| 7,564,469 B2 | 7/2009 | Cohen | |
| 7,565,295 B1 | 7/2009 | Hernandez-Rebollar | |
| 7,598,976 B2 | 10/2009 | Sofer et al. | |
| 7,618,260 B2 | 11/2009 | Daniel et al. | |
| D609,818 S | 2/2010 | Tsang et al. | |
| 7,656,290 B2 | 2/2010 | Fein et al. | |
| 7,659,915 B2 | 2/2010 | Kurzweil et al. | |
| 7,743,996 B2 | 6/2010 | Maciver | |
| D625,427 S | 10/2010 | Lee | |
| 7,843,488 B2 | 11/2010 | Stapleton | |
| 7,848,512 B2 | 12/2010 | Eldracher | |
| 7,864,991 B2 | 1/2011 | Espenlaub et al. | |
| 7,938,756 B2 | 5/2011 | Rodetsky et al. | |
| 7,991,576 B2 | 8/2011 | Roumeliotis | |
| 8,005,263 B2 | 8/2011 | Fujimura | |
| 8,035,519 B2 | 10/2011 | Davis | |
| D649,655 S | 11/2011 | Petersen | |
| 8,123,660 B2 | 2/2012 | Kruse et al. | |
| D656,480 S | 3/2012 | McManigal et al. | |
| 8,138,907 B2 | 3/2012 | Barbeau et al. | |
| 8,150,107 B2 | 4/2012 | Kurzweil et al. | |
| 8,177,705 B2 | 5/2012 | Abolfathi | |
| 8,239,032 B2 | 8/2012 | Dewhurst | |
| 8,253,760 B2 | 8/2012 | Sako et al. | |
| 8,300,862 B2 | 10/2012 | Newton et al. | |
| 8,325,263 B2 | 12/2012 | Kato et al. | |
| D674,501 S | 1/2013 | Petersen | |
| 8,359,122 B2 | 1/2013 | Koselka et al. | |
| 8,395,968 B2 | 3/2013 | Vartanian et al. | |
| 8,401,785 B2 | 3/2013 | Cho et al. | |
| 8,414,246 B2 | 4/2013 | Tobey | |
| 8,418,705 B2 | 4/2013 | Ota et al. | |
| 8,428,643 B2 | 4/2013 | Lin | |
| 8,483,956 B2 | 7/2013 | Zhang | |
| 8,494,507 B1 | 7/2013 | Tedesco et al. | |
| 8,494,859 B2 | 7/2013 | Said | |
| 8,538,687 B2 | 9/2013 | Plocher et al. | |
| 8,538,688 B2 | 9/2013 | Prehofer | |
| 8,571,860 B2 | 10/2013 | Strope | |
| 8,583,282 B2 | 11/2013 | Angle et al. | |
| 8,588,464 B2 | 11/2013 | Albertson et al. | |
| 8,588,972 B2 | 11/2013 | Fung | |
| 8,594,935 B2 | 11/2013 | Cioffi et al. | |
| 8,606,316 B2 | 12/2013 | Evanitsky | |
| 8,610,879 B2 | 12/2013 | Ben-Moshe et al. | |
| 8,630,633 B1 | 1/2014 | Tedesco et al. | |
| 8,676,274 B2 | 3/2014 | Li | |
| 8,676,623 B2 | 3/2014 | Gale et al. | |
| 8,694,251 B2 | 4/2014 | Janardhanan et al. | |
| 8,704,902 B2 | 4/2014 | Naick et al. | |
| 8,743,145 B1 | 6/2014 | Price | |
| 8,750,898 B2 | 6/2014 | Haney | |
| 8,768,071 B2 | 7/2014 | Tsuchinaga et al. | |
| 8,786,680 B2 | 7/2014 | Shiratori | |
| 8,797,141 B2 | 8/2014 | Best et al. | |
| 8,797,386 B2 | 8/2014 | Chou et al. | |
| 8,803,699 B2 | 8/2014 | Foshee et al. | |
| 8,814,019 B2 | 8/2014 | Dyster et al. | |
| 8,825,398 B2 | 9/2014 | Alexandre | |
| 8,836,532 B2 | 9/2014 | Fish, Jr. et al. | |
| 8,836,580 B2 | 9/2014 | Mendelson | |
| 8,836,910 B2 | 9/2014 | Cashin et al. | |
| 8,902,303 B2 | 12/2014 | Na'Aman et al. | |
| 8,909,534 B1 | 12/2014 | Heath | |
| D721,673 S | 1/2015 | Park et al. | |
| 8,926,330 B2 | 1/2015 | Taghavi | |
| 8,930,458 B2 | 1/2015 | Lewis et al. | |
| 8,981,682 B2 | 3/2015 | Delson et al. | |
| D727,194 S | 4/2015 | Wilson | |
| 9,004,330 B2 | 4/2015 | White | |
| 9,025,016 B2 | 5/2015 | Wexler et al. | |
| 9,053,094 B2 | 6/2015 | Yassa | |
| 9,076,450 B1 | 7/2015 | Sadek | |
| 9,081,079 B2 | 7/2015 | Chao et al. | |
| 9,081,385 B1 | 7/2015 | Ferguson | |
| D736,741 S | 8/2015 | Katz | |
| 9,111,545 B2 | 8/2015 | Jadhav et al. | |
| D738,238 S | 9/2015 | Pede et al. | |
| 9,137,484 B2 | 9/2015 | DiFrancesco et al. | |
| 9,137,639 B2 | 9/2015 | Garin et al. | |
| 9,140,554 B2 | 9/2015 | Jerauld | |
| 9,148,191 B2 | 9/2015 | Teng et al. | |
| 9,158,378 B2 | 10/2015 | Hirukawa | |
| D742,535 S | 11/2015 | Wu | |
| D743,933 S | 11/2015 | Park et al. | |
| 9,190,058 B2 | 11/2015 | Klein | |
| 9,230,430 B2 | 1/2016 | Civelli et al. | |
| 9,232,366 B1 | 1/2016 | Charlier et al. | |
| 9,267,801 B2 | 2/2016 | Gupta et al. | |
| 9,269,015 B2 | 2/2016 | Boncyk | |

(56) References Cited

U.S. PATENT DOCUMENTS

| | | |
|---|---|---|
| 9,304,588 B2 | 4/2016 | Aldossary |
| D756,958 S | 5/2016 | Lee et al. |
| D756,959 S | 5/2016 | Lee et al. |
| 9,335,175 B2 | 5/2016 | Zhang et al. |
| 9,341,014 B2 | 5/2016 | Oshima et al. |
| 9,355,547 B2 | 5/2016 | Stevens et al. |
| 2001/0023387 A1 | 9/2001 | Rollo |
| 2002/0067282 A1 | 6/2002 | Moskowitz et al. |
| 2002/0071277 A1 | 6/2002 | Starner et al. |
| 2002/0075323 A1 | 6/2002 | O'Dell |
| 2002/0173346 A1 | 11/2002 | Wang |
| 2002/0178344 A1 | 11/2002 | Bourguet |
| 2003/0026461 A1 | 2/2003 | Arthur Hunter |
| 2003/0133085 A1 | 7/2003 | Tretiakoff |
| 2003/0179133 A1 | 9/2003 | Pepin et al. |
| 2004/0232179 A1 | 11/2004 | Chauhan |
| 2004/0267442 A1 | 12/2004 | Fehr et al. |
| 2005/0208457 A1 | 9/2005 | Fink et al. |
| 2005/0221260 A1 | 10/2005 | Kikuchi |
| 2006/0004512 A1 | 1/2006 | Herbst |
| 2006/0028550 A1 | 2/2006 | Palmer |
| 2006/0029256 A1 | 2/2006 | Miyoshi |
| 2006/0129308 A1 | 6/2006 | Kates |
| 2006/0171704 A1 | 8/2006 | Bingle et al. |
| 2006/0177086 A1 | 8/2006 | Rye et al. |
| 2006/0184318 A1 | 8/2006 | Yoshimine |
| 2006/0292533 A1 | 12/2006 | Selod |
| 2007/0001904 A1 | 1/2007 | Mendelson |
| 2007/0052672 A1 | 3/2007 | Ritter et al. |
| 2007/0173688 A1 | 7/2007 | Kim |
| 2007/0296572 A1 | 12/2007 | Fein |
| 2008/0024594 A1 | 1/2008 | Ritchey |
| 2008/0068559 A1 | 3/2008 | Howell |
| 2008/0120029 A1 | 5/2008 | Zelek et al. |
| 2008/0145822 A1 | 6/2008 | Bucchieri |
| 2008/0174676 A1 | 7/2008 | Squilla et al. |
| 2008/0198222 A1 | 8/2008 | Gowda |
| 2008/0198324 A1 | 8/2008 | Fuziak |
| 2008/0251110 A1 | 10/2008 | Pede |
| 2008/0260210 A1 | 10/2008 | Kobeli |
| 2009/0012788 A1 | 1/2009 | Gilbert |
| 2009/0040215 A1 | 2/2009 | Afzulpurkar |
| 2009/0118652 A1 | 5/2009 | Carlucci |
| 2009/0122161 A1 | 5/2009 | Bolkhovitinov |
| 2009/0122648 A1 | 5/2009 | Mountain et al. |
| 2009/0157302 A1 | 6/2009 | Tashev et al. |
| 2009/0177437 A1 | 7/2009 | Roumeliotis |
| 2009/0189974 A1 | 7/2009 | Deering |
| 2010/0041378 A1 | 2/2010 | Aceves |
| 2010/0109918 A1 | 5/2010 | Liebermann |
| 2010/0110368 A1 | 5/2010 | Chaum |
| 2010/0179452 A1* | 7/2010 | Srinivasan .......... G06F 19/3418 600/595 |
| 2010/0182242 A1 | 7/2010 | Fields et al. |
| 2010/0182450 A1 | 7/2010 | Kumar |
| 2010/0198494 A1 | 8/2010 | Chao |
| 2010/0199232 A1 | 8/2010 | Mistry et al. |
| 2010/0241350 A1 | 9/2010 | Cioffi et al. |
| 2010/0245585 A1 | 9/2010 | Fisher et al. |
| 2010/0267276 A1 | 10/2010 | Wu |
| 2010/0292917 A1* | 11/2010 | Emam .................. A61H 3/061 701/533 |
| 2010/0298976 A1 | 11/2010 | Sugihara et al. |
| 2010/0305845 A1 | 12/2010 | Alexandre et al. |
| 2010/0308999 A1 | 12/2010 | Chornenky |
| 2011/0066383 A1 | 3/2011 | Jangle |
| 2011/0071830 A1 | 3/2011 | Kim |
| 2011/0092249 A1 | 4/2011 | Evanitsky |
| 2011/0124383 A1 | 5/2011 | Garra et al. |
| 2011/0181422 A1 | 7/2011 | Tran |
| 2011/0187640 A1 | 8/2011 | Jacobsen |
| 2011/0211760 A1 | 9/2011 | Boncyk |
| 2011/0216006 A1 | 9/2011 | Litschel |
| 2011/0221670 A1 | 9/2011 | King, III et al. |
| 2011/0260681 A1 | 10/2011 | Guccione |
| 2011/0307172 A1 | 12/2011 | Jadhav et al. |
| 2012/0016578 A1 | 1/2012 | Coppens |
| 2012/0053826 A1* | 3/2012 | Slamka .................. G01S 19/14 701/301 |
| 2012/0062357 A1 | 3/2012 | Slamka |
| 2012/0069511 A1 | 3/2012 | Azera |
| 2012/0075168 A1 | 3/2012 | Osterhout et al. |
| 2012/0085377 A1 | 4/2012 | Trout |
| 2012/0092161 A1 | 4/2012 | West |
| 2012/0092460 A1 | 4/2012 | Mahoney |
| 2012/0123784 A1 | 5/2012 | Baker et al. |
| 2012/0136666 A1 | 5/2012 | Corpier et al. |
| 2012/0143495 A1 | 6/2012 | Dantu |
| 2012/0162423 A1 | 6/2012 | Xiao et al. |
| 2012/0194552 A1 | 8/2012 | Osterhout et al. |
| 2012/0206335 A1 | 8/2012 | Osterhout et al. |
| 2012/0206607 A1 | 8/2012 | Morioka |
| 2012/0207356 A1 | 8/2012 | Murphy |
| 2012/0214418 A1 | 8/2012 | Lee |
| 2012/0220234 A1 | 8/2012 | Abreu |
| 2012/0232430 A1 | 9/2012 | Boissy et al. |
| 2012/0249797 A1 | 10/2012 | Haddick et al. |
| 2012/0252483 A1 | 10/2012 | Farmer et al. |
| 2012/0316884 A1 | 12/2012 | Rozaieski et al. |
| 2012/0323485 A1 | 12/2012 | Mutoh |
| 2012/0327194 A1 | 12/2012 | Shiratori |
| 2013/0002452 A1 | 1/2013 | Lauren |
| 2013/0044005 A1 | 2/2013 | Foshee et al. |
| 2013/0046541 A1 | 2/2013 | Klein et al. |
| 2013/0066636 A1 | 3/2013 | Singhal |
| 2013/0079061 A1 | 3/2013 | Jadhav |
| 2013/0115579 A1 | 5/2013 | Taghavi |
| 2013/0116559 A1 | 5/2013 | Levin |
| 2013/0127980 A1 | 5/2013 | Haddick |
| 2013/0128051 A1 | 5/2013 | Velipasalar et al. |
| 2013/0131985 A1 | 5/2013 | Weiland et al. |
| 2013/0141576 A1 | 6/2013 | Lord et al. |
| 2013/0155474 A1 | 6/2013 | Roach et al. |
| 2013/0157230 A1 | 6/2013 | Morgan |
| 2013/0184982 A1 | 7/2013 | DeLuca |
| 2013/0202274 A1 | 8/2013 | Chan |
| 2013/0211718 A1 | 8/2013 | Yoo et al. |
| 2013/0218456 A1 | 8/2013 | Zelek et al. |
| 2013/0228615 A1 | 9/2013 | Gates et al. |
| 2013/0229669 A1 | 9/2013 | Smits |
| 2013/0245396 A1 | 9/2013 | Berman et al. |
| 2013/0250078 A1* | 9/2013 | Levy .................... A61F 9/08 348/62 |
| 2013/0250233 A1 | 9/2013 | Blum et al. |
| 2013/0253818 A1 | 9/2013 | Sanders et al. |
| 2013/0271584 A1 | 10/2013 | Wexler et al. |
| 2013/0290909 A1* | 10/2013 | Gray ................... G01C 21/00 715/854 |
| 2013/0307842 A1 | 11/2013 | Grinberg et al. |
| 2013/0311179 A1 | 11/2013 | Wagner |
| 2013/0328683 A1 | 12/2013 | Sitbon et al. |
| 2013/0332452 A1 | 12/2013 | Jarvis |
| 2014/0009561 A1 | 1/2014 | Sutherland |
| 2014/0031081 A1 | 1/2014 | Vossoughi |
| 2014/0031977 A1 | 1/2014 | Goldenberg et al. |
| 2014/0032596 A1 | 1/2014 | Fish et al. |
| 2014/0037149 A1* | 2/2014 | Zetune ................. G01C 21/20 382/114 |
| 2014/0071234 A1 | 3/2014 | Millett |
| 2014/0081631 A1 | 3/2014 | Zhu et al. |
| 2014/0085446 A1 | 3/2014 | Hicks |
| 2014/0098018 A1 | 4/2014 | Kim et al. |
| 2014/0100773 A1 | 4/2014 | Cunningham et al. |
| 2014/0125700 A1 | 5/2014 | Ramachandran |
| 2014/0132388 A1 | 5/2014 | Alalawi |
| 2014/0133290 A1 | 5/2014 | Yokoo |
| 2014/0184384 A1 | 7/2014 | Zhu et al. |
| 2014/0222023 A1 | 8/2014 | Kim et al. |
| 2014/0251396 A1 | 9/2014 | Subhashrao et al. |
| 2014/0253702 A1 | 9/2014 | Wexler |
| 2014/0278070 A1 | 9/2014 | McGavran |
| 2014/0281943 A1 | 9/2014 | Prilepov |
| 2014/0287382 A1 | 9/2014 | Villar Cloquell |

(56) References Cited

U.S. PATENT DOCUMENTS

| | | | |
|---|---|---|---|
| 2014/0309806 A1* | 10/2014 | Ricci | B60Q 1/00 701/1 |
| 2014/0313040 A1 | 10/2014 | Wright, Sr. | |
| 2014/0335893 A1 | 11/2014 | Ronen | |
| 2014/0343846 A1 | 11/2014 | Goldman et al. | |
| 2014/0345956 A1 | 11/2014 | Kojina | |
| 2014/0347265 A1* | 11/2014 | Aimone | G09G 3/003 345/156 |
| 2014/0368412 A1 | 12/2014 | Jacobsen | |
| 2014/0369541 A1 | 12/2014 | Miskin | |
| 2014/0379336 A1 | 12/2014 | Bhatnager | |
| 2015/0002808 A1 | 1/2015 | Rizzo, III et al. | |
| 2015/0016035 A1 | 1/2015 | Tussy | |
| 2015/0063661 A1* | 3/2015 | Lee | G06F 3/011 382/124 |
| 2015/0081884 A1 | 3/2015 | Maguire | |
| 2015/0099946 A1 | 4/2015 | Sahin | |
| 2015/0109107 A1 | 4/2015 | Gomez et al. | |
| 2015/0120186 A1* | 4/2015 | Heikes | G01C 22/006 701/468 |
| 2015/0125831 A1 | 5/2015 | Chandrashekhar Nair et al. | |
| 2015/0141085 A1 | 5/2015 | Nuovo et al. | |
| 2015/0142891 A1 | 5/2015 | Haque | |
| 2015/0154643 A1 | 6/2015 | Artman et al. | |
| 2015/0196101 A1 | 7/2015 | Dayal et al. | |
| 2015/0198454 A1 | 7/2015 | Moore et al. | |
| 2015/0198455 A1 | 7/2015 | Chen | |
| 2015/0199566 A1 | 7/2015 | Moore et al. | |
| 2015/0201181 A1 | 7/2015 | Moore et al. | |
| 2015/0211858 A1 | 7/2015 | Jerauld | |
| 2015/0219757 A1 | 8/2015 | Boelter et al. | |
| 2015/0223355 A1 | 8/2015 | Fleck | |
| 2015/0256977 A1* | 9/2015 | Huang | H04W 4/028 455/456.3 |
| 2015/0257555 A1 | 9/2015 | Wong | |
| 2015/0260474 A1 | 9/2015 | Rublowsky | |
| 2015/0262509 A1 | 9/2015 | Labbe | |
| 2015/0279172 A1* | 10/2015 | Hyde | G06Q 10/10 340/815.4 |
| 2015/0330787 A1 | 11/2015 | Cioffi et al. | |
| 2015/0336276 A1 | 11/2015 | Song | |
| 2015/0341591 A1 | 11/2015 | Kelder et al. | |
| 2015/0346496 A1 | 12/2015 | Haddick et al. | |
| 2015/0356837 A1 | 12/2015 | Pajestka | |
| 2015/0364943 A1 | 12/2015 | Vick | |
| 2015/0367176 A1* | 12/2015 | Bejestan | G06F 19/3481 482/9 |
| 2015/0375395 A1 | 12/2015 | Kwon | |
| 2016/0007158 A1* | 1/2016 | Venkatraman | H04W 4/023 455/456.2 |
| 2016/0028917 A1 | 1/2016 | Wexler | |
| 2016/0042228 A1 | 2/2016 | Opalka | |
| 2016/0098138 A1 | 4/2016 | Park | |
| 2016/0156850 A1 | 6/2016 | Werblin et al. | |
| 2016/0198319 A1* | 7/2016 | Huang | H04L 67/26 455/412.2 |

FOREIGN PATENT DOCUMENTS

| | | |
|---|---|---|
| CN | 201440733 | 4/2010 |
| CN | 101803988 | 8/2010 |
| CN | 101647745 | 1/2011 |
| CN | 102316193 | 1/2012 |
| CN | 102631280 | 8/2012 |
| CN | 202547659 | 11/2012 |
| CN | 202722736 | 2/2013 |
| CN | 102323819 | 6/2013 |
| CN | 103445920 | 12/2013 |
| DE | 102011080056 | 1/2013 |
| DE | 102012000587 | 7/2013 |
| DE | 102012202614 | 8/2013 |
| EP | 1174049 | 9/2004 |
| EP | 1721237 | 11/2006 |
| EP | 2368455 | 9/2011 |
| EP | 2371339 | 10/2011 |
| EP | 2127033 | 8/2012 |
| EP | 2581856 | 4/2013 |
| EP | 2751775 | 7/2016 |
| FR | 2885251 | 11/2006 |
| GB | 2401752 | 11/2004 |
| JP | 1069539 | 3/1998 |
| JP | 2001304908 | 10/2001 |
| JP | 201012529 | 1/2010 |
| JP | 2010182193 | 8/2010 |
| JP | 2013169611 | 9/2013 |
| KR | 100405636 | 11/2003 |
| KR | 20080080688 | 9/2008 |
| KR | 20120020212 | 3/2012 |
| KR | 1250929 | 4/2013 |
| WO | WO9504440 | 2/1995 |
| WO | WO 9949656 | 9/1999 |
| WO | WO 0010073 | 2/2000 |
| WO | WO 0038393 | 6/2000 |
| WO | WO 0179956 | 10/2001 |
| WO | WO 2004/076974 | 9/2004 |
| WO | WO 2006/028354 | 3/2006 |
| WO | WO 2006/045819 | 5/2006 |
| WO | WO 2007/031782 | 3/2007 |
| WO | WO 2008/008791 | 1/2008 |
| WO | WO 2008015375 | 2/2008 |
| WO | WO 2008/035993 | 3/2008 |
| WO | WO 2008/096134 | 8/2008 |
| WO | WO2008127316 | 10/2008 |
| WO | WO 2010/062481 | 6/2010 |
| WO | WO 2010/109313 | 9/2010 |
| WO | WO 2012/040703 | 3/2012 |
| WO | WO2012163675 | 12/2012 |
| WO | WO 2013/045557 | 4/2013 |
| WO | WO 2013/054257 | 4/2013 |
| WO | WO 2013/067539 | 5/2013 |
| WO | WO 2013/147704 | 10/2013 |
| WO | WO 2014104531 | 7/2014 |
| WO | WO 2014/138123 | 9/2014 |
| WO | WO 2014/172378 | 10/2014 |
| WO | WO 2015065418 | 5/2015 |
| WO | WO2015092533 | 6/2015 |
| WO | WO 2015108882 | 7/2015 |
| WO | WO2015127062 | 8/2015 |

OTHER PUBLICATIONS

Cardonha et al.; "*A Crowdsourcing Platform for the Construction of Accessibility Maps*"; W4A'13 Proceedings of the 10$^{th}$ International Cross-Disciplinary Conference on Web Accessibility; Article No. 26; 2013; 5 pages.

Bujacz et al.; "*Remote Guidance for the Blind—A Proposed Teleassistance System and Navigation Trials*"; Conference on Human System Interactions; May 25-27, 2008; 6 pages.

Rodriguez et al; "*CrowdSight: Rapidly Prototyping Intelligent Visual Processing Apps*"; AAAI Human Computation Workshop (HCOMP); 2011; 6 pages.

Chaudary et al.; "*Alternative Navigation Assistance Aids for Visually Impaired Blind Persons*"; Proceedings of ICEAPVI; Feb. 12-14, 2015; 5 pages.

Garaj et al.; "*A System for Remote Sighted Guidance of Visually Impaired Pedestrians*"; The British Journal of Visual Impairment; vol. 21, No. 2, 2003; 9 pages.

Coughlan et al.; "*Crosswatch: A System for Providing Guidance to Visually Impaired Travelers at Traffic Intersections*"; Journal of Assistive Technologies 7.2; 2013; 17 pages.

Sudol et al.; "*LookTel—A Comprehensive Platform for Computer-Aided Visual Assistance*"; Computer Vision and Pattern Recognition Workshops (CVPRW), 2010 IEEE Computer Society Conference; Jun. 13-18, 2010; 8 pages.

Paladugu et al.; "*GoingEasy® with Crowdsourcing in the Web 2.0 World for Visually Impaired Users: Design and User Study*"; Arizona State University; 8 pages.

Kammoun et al.; "*Towards a Geographic Information System Facilitating Navigation of Visually Impaired Users*"; Springer Berlin Heidelberg; 2012; 8 pages.

(56) References Cited

OTHER PUBLICATIONS

Bigham et al.; "VizWiz: Nearly Real-Time Answers to Visual Questions" Proceedings of the 23nd annual ACM symposium on User interface software and technology; 2010; 2 pages.
Guy et al; "CrossingGuard: Exploring Information Content in Navigation Aids for Visually Impaired Pedestrians" Proceedings of the SIGCHI Conference on Human Factors in Computing Systems; May 5-10, 2012; 10 pages.
Borenstein et al.; "The GuideCane—A Computerized Travel Aid for the Active Guidance of Blind Pedestrians"; IEEE International Conference on Robotics and Automation; Apr. 21-27, 1997; 6 pages.
Bhatlawande et al.; "Way-finding Electronic Bracelet for Visually Impaired People"; IEEE Point-of-Care Healthcare Technologies (PHT), Jan. 16-18, 2013; 4 pages.
Blenkhorn et al.; "An Ultrasonic Mobility Device with Minimal Audio Feedback"; Center on Disabilities Technology and Persons with Disabilities Conference; Nov. 22, 1997; 5 pages.
Mann et al.; "Blind Navigation with a Wearable Range Camera and Vibrotactile Helmet"; 19th ACM International Conference on Multimedia; Nov. 28, 2011; 4 pages.
Shoval et al.; "The Navbelt—A Computerized Travel Aid for the Blind"; RESNA Conference, Jun. 12-17, 1993; 6 pages.
Kumar et al.; "An Electronic Travel Aid for Navigation of Visually Impaired Persons"; Communications Systems and Networks (COMSNETS), 2011 Third International Conference; Jan. 2011; 5 pages.
Pawar et al.; "Multitasking Stick for Indicating Safe Path to Visually Disable People"; IOSR Journal of Electronics and Communication Engineering (IOSR-JECE), vol. 10, Issue 3, Ver. II; May-Jun 2015; 5 pages.
Pagliarini et al.; "Robotic Art for Wearable"; Proceedings of EUROSIAM: European Conference for the Applied Mathematics and Informatics 2010; 10 pages.
Greenberg et al.; "Finding Your Way: A Curriculum for Teaching and Using the Braillenote with Sendero GPS 2011"; California School for the Blind; 2011; 190 pages.
Helal et al.; "Drishti: An Integrated Navigation System for Visually Impaired and Disabled"; Fifth International Symposium on Wearable Computers; Oct. 8-9, 2001; 8 pages.
Parkes, Don; "Audio Tactile Systems for Designing and Learning Complex Environments as a Vision Impaired Person: Static and Dynamic Spatial Information Access"; EdTech-94 Proceedings; 1994; 8 pages.
Zeng et al.; "Audio-Haptic Browser for a Geographical Information System"; ICCHP 2010, Part II, LNCS 6180; Jul. 14-16, 2010; 8 pages.
AlZuhair et al.; "NFC Based Applications for Visually Impaired People—A Review"; IEEE International Conference on Multimedia and Expo Workshops (ICMEW), Jul. 14, 2014; 7 pages.
Graf, Christian; "Verbally Annotated Tactile Maps—Challenges and Approaches"; Spatial Cognition VII, vol. 6222; Aug. 15-19, 2010; 16 pages.
Hamid, Nazatul Naquiah Abd; "Facilitating Route Learning Using Interactive Audio-Tactile Maps for Blind and Visually Impaired People"; CHI 2013 Extended Abstracts; Apr. 27, 2013; 6 pages.
Ramya, et al.; "Voice Assisted Embedded Navigation System for the Visually Impaired"; International Journal of Computer Applications; vol. 64, No. 13, Feb. 2013; 7 pages.
Caperna et al.; "A Navigation and Object Location Device for the Blind"; Tech. rep. University of Maryland College Park; May 2009; 129 pages.
Burbey et al.; "Human Information Processing with the Personal Memex"; ISE 5604 Fall 2005; Dec. 6, 2005; 88 pages.
Ghiani, et al.; "Vibrotactile Feedback to Aid Blind Users of Mobile Guides"; Journal of Visual Languages and Computing 20; 2009; 13 pages.
Guerrero et al.; "An Indoor Navigation System for the Visually Impaired"; Sensors vol. 12, Issue 6; Jun. 13, 2012; 23 pages.

Nordin et al.; "Indoor Navigation and Localization for Visually Impaired People Using Weighted Topological Map"; Journal of Computer Science vol. 5, Issue 11; 2009; 7 pages.
Hesch et al.; "Design and Analysis of a Portable Indoor Localization Aid for the Visually Impaired"; International Journal of Robotics Research; vol. 29; Issue 11; Sep. 2010; 15 pgs.
Joseph et al.; "Visual Semantic Parameterization—To Enhance Blind User Perception for Indoor Navigation"; Multimedia and Expo Workshops (ICMEW), 2013 IEEE International Conference; Jul. 15, 2013; 7 pages.
Katz et al; "NAVIG: Augmented Reality Guidance System for the Visually Impaired"; Virtual Reality (2012) vol. 16; 2012; 17 pages.
Rodríguez et al.; "Assisting the Visually Impaired: Obstacle Detection and Warning System by Acoustic Feedback"; Sensors 2012; vol. 12; 21 pages.
Treuillet; "Outdoor/Indoor Vision-Based Localization for Blind Pedestrian Navigation Assistance"; WSPC/Instruction File; May 23, 2010; 16 pages.
Ran et al.; "Drishti: An Integrated Indoor/Outdoor Blind Navigation System and Service"; Proceeding PERCOM '04 Proceedings of the Second IEEE International Conference on Pervasive Computing and Communications (PerCom'04); 2004; 9 pages.
Wang, et al.; "Camera-Based Signage Detection and Recognition for Blind Persons"; 13th International Conference (ICCHP) Part 2 Proceedings; Jul. 11-13, 2012; 9 pages.
Krishna et al.; "A Systematic Requirements Analysis and Development of an Assistive Device to Enhance the Social Interaction of People Who are Blind or Visually Impaired"; Workshop on Computer Vision Applications for the Visually Impaired; Marseille, France; 2008; 12 pages.
Lee et al.; "A Walking Guidance System for the Visually Impaired"; International Journal of Pattern Recognition and Artificial Intelligence; vol. 22; No. 6; 2008; 16 pages.
Ward et al.; "Visual Experiences in the Blind Induced by an Auditory Sensory Substitution Device"; Journal of Consciousness and Cognition; Oct. 2009; 30 pages.
Merino-Garcia, et al.; "A Head-Mounted Device for Recognizing Text in Natural Sciences"; CBDAR'11 Proceedings of the 4th International Conference on Camera-Based Document Analysis and Recognition; Sep. 22, 2011; 7 pages.
Yi, Chucai; "Assistive Text Reading from Complex Background for Blind Persons"; CBDAR'11 Proceedings of the 4th International Conference on Camera-Based Document Analysis and Recognition; Sep. 22, 2011; 7 pages.
Yang, et al.; "Towards Automatic Sign Translation"; The Interactive Systems Lab, Carnegie Mellon University; 2001; 5 pages.
Meijer, Dr. Peter B.L.; "Mobile OCR, Face and Object Recognition for the Blind"; The vOICe, www.seeingwithsound.com/ocr.htm; Apr. 18, 2014; 7 pages.
Omron; Optical Character Recognition Sensor User's Manual; 2012; 450 pages.
Park, Sungwoo; "Voice Stick"; www.yankodesign.com/2008/08/21/voice-stick; Aug. 21, 2008; 4 pages.
Rentschler et al.; "Intelligent Walkers for the Elderly: Performance and Safety Testing of VA-PAMAID Robotic Walker"; Department of Veterans Affairs Journal of Rehabilitation Research and Development; vol. 40, No. 5; Sep./Oct. 2013; 9pages.
Science Daily; "Intelligent Walker Designed to Assist the Elderly and People Undergoing Medical Rehabilitation"; http://www.sciencedaily.com/releases/2008/11/081107072015.htm; Jul. 22, 2014; 4 pages.
Glover et al.; "A Robotically-Augmented Walker for Older Adults"; Carnegie Mellon University, School of Computer Science; Aug. 1, 2003; 13 pages.
OrCam; www.orcam.com; Jul. 22, 2014; 3 pages.
Eccles, Lisa; "Smart Walker Detects Obstacles"; Electronic Design; http://electronicdesign.com/electromechanical/smart-walker-detects-obstacles; Aug. 20, 2001; 2 pages.
Graft, Birgit; "An Adaptive Guidance System for Robotic Walking Aids"; Journal of Computing and Information Technology—CIT 17; 2009; 12 pages.

(56) References Cited

OTHER PUBLICATIONS

Frizera et al.; "*The Smart Walkers as Geriatric Assistive Device. The SIMBIOSIS Purpose*"; Gerontechnology, vol. 7, No. 2; Jan. 30, 2008; 6 pages.

Rodriquez-Losada et al.; "*Guido, The Robotic Smart Walker for the Frail Visually Impaired*"; IEEE International Conference on Robotics and Automation (ICRA); Apr. 18-22, 2005; 15 pages.

Kayama et al.; "*Outdoor Environment Recognition and Semi-Autonomous Mobile Vehicle for Supporting Mobility of the Elderly and Disabled People*"; National Institute of Information and Communications Technology, vol. 54, No. 3; Aug. 2007; 11 pages.

Kalra et al.; "*A Braille Writing Tutor to Combat Illiteracy in Developing Communities*"; Carnegie Mellon University Research Showcase, Robotics Institute; 2007; 10 pages.

Blaze Engineering; "*Visually Impaired Resource Guide: Assistive Technology for Students who use Braille*"; Braille 'n Speak Manual; http://www.blaize.com; Nov. 17, 2014; 5 pages.

AppleVis; *An Introduction to Braille Screen Input on iOS 8*; http://www.applevis.com/guides/braille-ios/introduction-braille-screen-input-ios-8, Nov. 16, 2014; 7 pages.

Dias et al.; "*Enhancing an Automated Braille Writing Tutor*"; IEEE/RSJ International Conference on Intelligent Robots and Systems; Oct. 11-15, 2009; 7 pages.

D'Andrea, Frances Mary; "*More than a Perkins Brailler: A Review of the Mountbatten Brailler, Part 1*"; AFB AccessWorld Magazine; vol. 6, No. 1, Jan. 2005; 9 pages.

Trinh et al.; "*Phoneme-based Predictive Text Entry Interface*"; Proceedings of the 16th International ACM SIGACCESS Conference on Computers & Accessibility; Oct. 2014; 2 pgs.

Merri et al.; "*The Instruments for a Blind Teacher of English: The challenge of the board*"; European Journal of Psychology of Education, vol. 20, No. 4 (Dec. 2005), 15 pages.

Kirinic et al.; "*Computers in Education of Children with Intellectual and Related Developmental Disorders*"; International Journal of Emerging Technologies in Learning, vol. 5, 2010, 9 pages.

Campos et al.; "*Design and Evaluation of a Spoken-Feedback Keyboard*"; Department of Information Systems and Computer Science, INESC-ID/IST/Universidade Tecnica de Lisboa, Jul. 2004; 6 pages.

Ebay; Matin (Made in Korea) Neoprene Canon DSLR Camera Curved Neck Strap #6782; http://www.ebay.com/itm/MATIN-Made-in-Korea-Neoprene-Canon-DSLR-Camera-Curved-Neck-Strap-6782-/281608526018?hash=item41912d18c2 :g:~pMAAOSwe-FU6zDa ; 4 pages.

Newegg; Motorola S10-HD Bluetooth Stereo Headphone w/ Comfortable Sweat Proof Design; http://www.newegg.com/Product/Product.aspx?Item=9SIA0NW2G39901&Tpk=9sia0nw2g39901; 4 pages.

Newegg; Motorola Behind the Neck Stereo Bluetooth Headphone Black/Red Bulk (S9)—OEM; http://www.newegg.com/Product/Product.aspx?Item=N82E16875982212&Tpk=n82e16875982212; 3 pages.

Zhang et al.; "A Multiple Sensor-Based Shoe-Mounted User Interface Designed for Navigation Systems for the Visually Impaired"; Wireless Internet Conference (WICON), 2010 the 5th Annual ICST; 8 pages; Mar. 1-3, 2010.

Shoval et al.; "Robotics-Based Obstacle-Avoidance Systems for the Blind and Visually Impaired"; IEEE Robotics & Automation Magazine; pp. 9-20; Mar. 2003.

Dowling et al.; "Intelligent image processing constraints for blind mobility facilitated through artificial vision"; pp. 109-114; 2003.

Heyes, Tony; "The Sonic Pathfinder"; http://members.optuszoo.com.au/aheyew40/pa/pf_blerf.html; 7 pages; Dec. 11, 2014.

Lee et al.; "Adaptive power control of obstacle avoidance system using via motion context for visually impaired person." *Cloud Computing and Social Networking (ICCCSN), 2012 International Conference on.* IEEE, 2012.

Wilson, Jeff, et al. "Swan: System for wearable audio navigation." *Wearable Computers, 2007 11th IEEE International Symposium on.* IEEE, 2007.

Bharathi et al.; "Effective Navigation for Visually Impaired by Wearable Obstacle Avoidance System;" *2012 International Conference on Computing, Electronics and Electrical Technologies (ICCEET);* pp. 956-958; 2012.

Pawar et al.; "Review Paper on Multitasking Stick for Guiding Safe Path for Visually Disable People;" *IJPRET;* vol. 3, No. 9; pp. 929-936; 2015.

Ram et al.; "The People Sensor: A Mobility Aid for the Visually Impaired;" 2012 16th International Symposium on Wearable Computers; pp. 166-167; 2012.

Singhal; "The Development of an Intelligent Aid for Blind and Old People;" *Emerging Trends and Applications in Computer Science (ICETACS), 2013 1st International Conference;* pp. 182-185; Sep. 13, 2013.

Aggarwal et al.; "All-in-One Companion for Visually Impaired;" *International Journal of Computer Applications;* vol. 79, No. 14; pp. 37-40; Oct. 2013.

"Light Detector" *EveryWare Technologies;* 2 pages; Jun. 18, 2016.

Arati et al. "Object Recognition in Mobile Phone Application for Visually Impaired Users;" *IOSR Journal of Computer Engineering (IOSR-JCE);* vol. 17, No. 1; pp. 30-33; Jan. 2015.

Yabu et al.; "Development of a Wearable Haptic Tactile Interface as an Aid for the Hearing and/or Visually Impaired;" *NTUT Education of Disabilities;* vol. 13; pp. 5-12; 2015.

Mau et al.; "BlindAid: An Electronic Travel Aid for the Blind;" *The Robotics Institute Carnegie Mellon University;* 27 pages; May 2008.

Shidujaman et al.; "Design and navigation Prospective for Wireless Power Transmission Robot;" IEEE; Jun. 2015.

Wu et al. "Fusing Multi-Modal Features for Gesture Recognition", Proceedings of the 15th ACM on International Conference on Multimodal Interaction, Dec. 9, 2013, ACM, pp. 453-459.

Pitsikalis et al. "Multimodal Gesture Recognition via Multiple Hypotheses Rescoring", Journal of Machine Learning Research, Feb. 2015, pp. 255-284.

Shen et al. "Walkie-Markie: Indoor Pathway Mapping Made Easy" 10th USENIX Symposium on Networked Systems Design and Implementation (NSDI'13); pp. 85-98, 2013.

Tu et al. "Crowdsourced Routing II D2.6" 34 pages; 2012.

De Choudhury et al. "Automatic Construction of Travel Itineraries Using Social Breadcrumbs" pp. 35-44; Jun. 2010.

\* cited by examiner

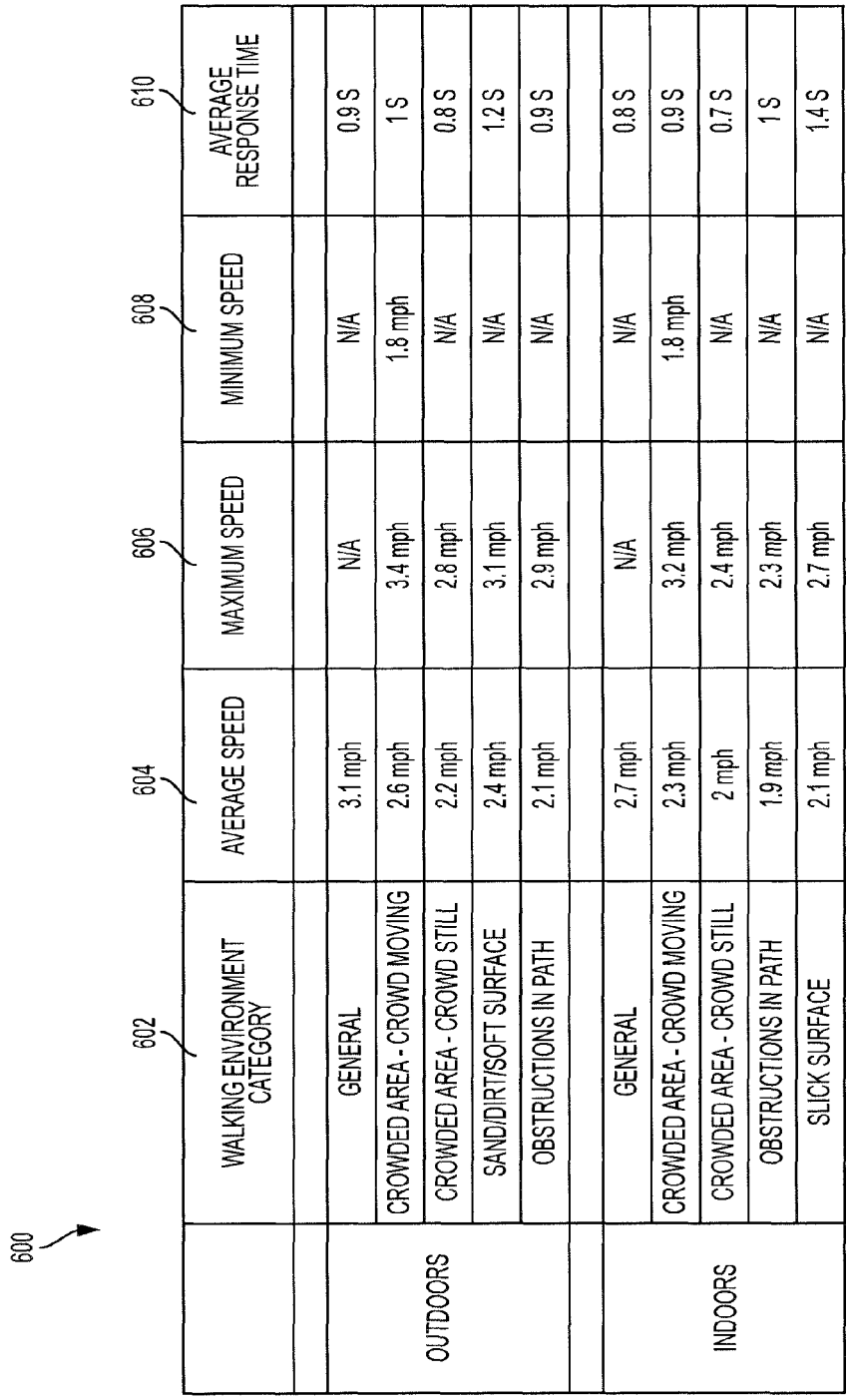

FIG. 6

| | WALKING ENVIRONMENT CATEGORY | AVERAGE SPEED | MAXIMUM SPEED | MINIMUM SPEED | AVERAGE RESPONSE TIME |
|---|---|---|---|---|---|
| OUTDOORS | GENERAL | 3.1 mph | N/A | N/A | 0.9 S |
| | CROWDED AREA - CROWD MOVING | 2.6 mph | 3.4 mph | 1.8 mph | 1 S |
| | CROWDED AREA - CROWD STILL | 2.2 mph | 2.8 mph | N/A | 0.8 S |
| | SAND/DIRT/SOFT SURFACE | 2.4 mph | 3.1 mph | N/A | 1.2 S |
| | OBSTRUCTIONS IN PATH | 2.1 mph | 2.9 mph | N/A | 0.9 S |
| INDOORS | GENERAL | 2.7 mph | N/A | N/A | 0.8 S |
| | CROWDED AREA - CROWD MOVING | 2.3 mph | 3.2 mph | 1.8 mph | 0.9 S |
| | CROWDED AREA - CROWD STILL | 2 mph | 2.4 mph | N/A | 0.7 S |
| | OBSTRUCTIONS IN PATH | 1.9 mph | 2.3 mph | N/A | 1 S |
| | SLICK SURFACE | 2.1 mph | 2.7 mph | N/A | 1.4 S |

SYSTEM AND METHOD FOR PROVIDING NAVIGATION INSTRUCTIONS AT OPTIMAL TIMES

BACKGROUND

1. Field

The present disclosure relates to a system and a method for providing navigation instructions, and more particularly to a system and a method for providing navigation instructions at optimal times.

2. Description of the Related Art

Navigation systems have been in use for years and are capable of providing navigation instructions to a user based on a current location and a desired destination. Typically, these navigation systems are used in cars for providing driving directions. These navigation systems utilize Global Positioning System (GPS) technology for estimating the current location of the car. GPS technology may, according to the United States Government, have an accuracy of a 7.8 meters variance with a 95% confidence level. High quality GPS technology may have a variance that is within 3.5 meters. This accuracy is typically sufficient for a vehicle as roads are typically at least a few meters wide and cars move at a rate that reduces the impact of a 3.5 meter variance.

These navigation systems may provide turning instructions as a driver approaches a turn. They may output the instructions a predetermined distance prior to a turn so that the driver can be notified of the turn prior to approaching the turn. Even considering the variance of the GPS technology, these instructions are typically provided with adequate time for the driver to prepare for and take the turn. This is because even if the GPS locates the vehicle 7.8 meters closer to the turn, the instruction will be provided to the user with sufficient time because 7.8 meters is negligible at most vehicle speeds.

More recently, portable navigation systems have been developed. For example, many smartphones and other mobile devices currently include navigation systems. Users can now use these portable navigation systems when riding a bike, walking or otherwise proceeding along a route at a slow speed relative to a car. These portable navigation systems, as the vehicle-based navigation systems, use GPS technology for estimating a current location of the navigation system. This technology is usually, but not always, adequate for this type of use as the navigation system can minimize the risk of a user missing a turn. This is because the navigation systems can output the instruction at a sufficiently large distance prior to the turn so that the user can look for the turn as he/she approaches the turn.

However, individuals having certain disabilities, such as blindness, cannot detect turns as they approach. In order for these individuals to gain the most benefit from a navigation system, the navigation system should output the instruction at an optimal time so that the user knows the exact moment for turning. A difference of even 3 meters can make a large impact on a disabled user's use of a navigation system. Therefore, navigation systems using solely GPS technology may not be usable or optimal for disabled users.

Thus, there is a need for systems and methods for providing navigation instructions to users at precise times.

SUMMARY

What is described is a wearable smart device for alerting a user of an upcoming turn or object. The wearable smart device includes a camera configured to detect image data. The wearable smart device also includes a processor coupled to the camera and configured to determine a current speed of the wearable smart device based on the image data. The processor is also configured to determine when a navigation instruction is to be output based on the current speed. The wearable smart device also includes an output unit coupled to the processor and configured to output the navigation instruction.

Also described is a wearable smart device for alerting a user of an upcoming turn or object. The wearable smart device includes a sensor configured to detect sensed data and a memory configured to store a first average speed. The wearable smart device also includes a processor coupled to the sensor and the memory. The processor is configured to determine a current speed based on the sensed data and to determine whether to set a selected speed equal to the first average speed or the current speed based on the sensed data. The processor is also configured to determine when a navigation instruction is to be output based on the selected speed. The wearable smart device also includes an output unit coupled to the processor and configured to output the navigation instruction.

Also described is a wearable smart device for alerting a user of an upcoming turn or object. The wearable smart device includes a sensor configured to detect sensed data. The wearable smart device also includes a memory configured to store a first average speed corresponding to a first walking environment and a second average speed corresponding to a second walking environment. The wearable smart device also includes a processor coupled to the sensor and the memory. The processor is configured to set a selected speed to be equal to the first average speed when a current walking environment of the wearable smart device corresponds to the first walking environment. The processor is also configured to set the selected speed to be equal to the second average speed when the current walking environment of the wearable smart device corresponds to the second walking environment. The processor is also configured to determine when the navigation instruction is to be output based on the selected speed. The wearable smart device also includes an output unit coupled to the processor and configured to output the navigation instruction.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIG. 6 illustrates an exemplary database for storing an average speed, a maximum speed and an average response time for various walking environments according to an embodiment of the present invention.

DETAILED DESCRIPTION

Disclosed herein are systems and methods for providing navigation instructions at optimal times. The systems and methods provide several benefits and advantages such as providing better navigation instructions to individuals, particularly disabled individuals, which increases the comfort, ease and safety of using a navigation system by these individuals. These benefits are achieved by outputting navigation instructions at optimal times so that disabled users can stop, move or change directions or speeds (e.g., make a turn) at precisely the right moment or time. Outputting navigation instructions at optimal times is achieved by the system determining when to provide the navigation instructions to the user based on the user's speed and by the positioning of the system being based on image data and/or IMU data instead of solely GPS data. Determining when to provide navigation instructions based on the user's speed provides benefits and advantages such as the ability to output instructions to a user based on individual characteristics of the user. This is advantageous because different users walk at different speeds, so a timing determined for one user may not be accurate for another user. Determining when to provide navigation instructions based on the user's speed provide additional benefits and advantages such as allowing the timing of the instructions to change as characteristics of the user change. The systems and methods provide additional benefits and advantages such as the instruction timing being tailored to various walking environments of the user such as a dirt path versus a paved path, indoors versus outdoors, etc., further allowing accurate timing of the instructions.

An exemplary system includes a camera capable of detecting image data corresponding to an environment of a user. The system further includes a memory that is capable of storing an average walking speed of the user. The memory is also capable of storing various walking speeds that each corresponds to a particular type of environment of the user. The system further includes a processor connected to the camera and the memory. The processor is capable of determining a current speed of the user based on the image data. The processor is also capable of updating the average walking speed based on the current speed. The processor is also capable of determining whether the system should provide a navigation instruction based on the average walking speed or the current walking speed. The processor is also capable of determining when to output the navigation instruction based on at least one of the average walking speed or the current walking speed.

Figure 1:
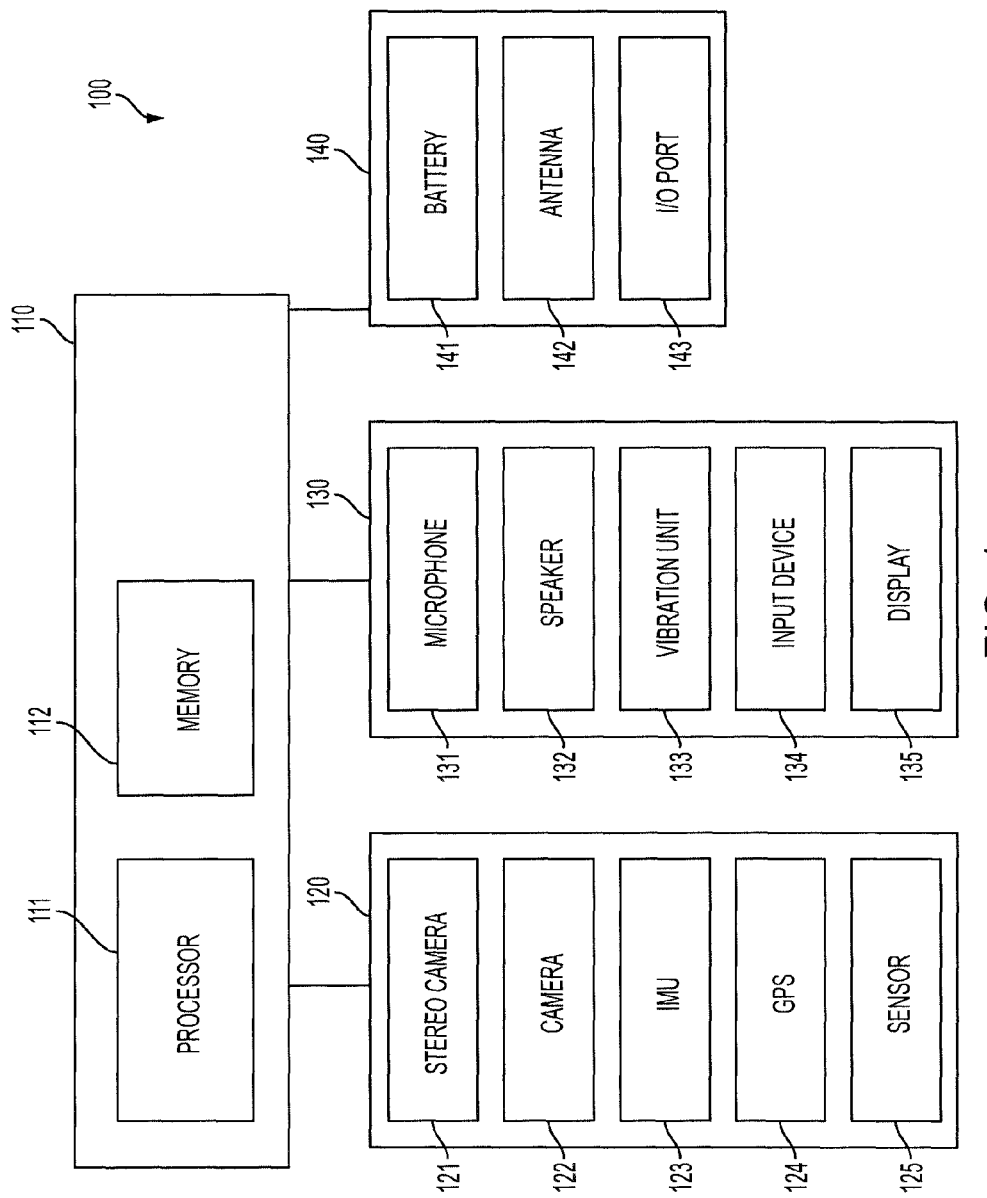
FIG. 1 is a block diagram of a wearable smart device capable of providing navigation instructions at optimal times according to an embodiment of the present invention.

In one implementation and with reference to FIG. 1, a wearable smart device 100 includes an onboard processing array 110 which communicates with a sensor array 120, an interface array 130 and a component array 140. The onboard processing array 110, the sensor array 120, the interface array 130 and the component array 140 are exemplary groupings to visually organize the components of the wearable smart device 100 in the block diagram of FIG. 1 and are not limiting or necessarily representative of any physical groupings. In addition, certain implementations may have more or less components than illustrated in FIG. 1.

The onboard processing array 110 includes a processor 111 and a memory 112. The processor 111 may be a computer processor such as an ARM processor, DSP processor, distributed processor or other form of central processing. The processor 111 may be positioned on the wearable smart device 100, may be a remote processor or it may be a pairing of a local and a remote processor.

The memory 112 may be one or any combination of the following: a RAM or other volatile or nonvolatile memory, a non-transitory memory or a data storage device, such as a hard disk drive, a solid state disk drive, a hybrid disk drive or other appropriate data storage. The memory 112 may further store machine-readable instructions which may be loaded into the memory 112 and executed by the processor 111. As with the processor 111, the memory 112 may be positioned on the wearable smart device 100, may be positioned remote from the wearable smart device 100 or may be a pairing of a local and a remote memory.

The sensor array 120 includes a pair of stereo cameras 121, a camera 122, an inertial measurement unit (IMU) 123, a global positioning system (GPS) 124 and a sensor 125. The stereo cameras 121 may be a stereo camera pair comprising two cameras offset by a stereo distance. The IMU 123 may be an IMU which may further comprise one or more of an accelerometer, a gyroscope, a magnetometer or the like. The GPS 124 may be one or more GPS units. The sensor 125 may be one or more sensors which provide further information about the environment in conjunction with the rest of the sensor array 120 such as one or more of a camera, a temperature sensor, an air pressure sensor, a moisture or humidity sensor, a gas detector or other chemical sensor, a sound sensor, a pH sensor, a smoke detector, a metal detector, an actinometer, an altimeter, a depth gauge, a compass, a radiation sensor, a motion detector, a light sensor or other sensor.

The interface array 130 includes a microphone 131, a speaker 132, a vibration unit 133, an input device 134 and a display 135. The microphone 131 may be a microphone or other device capable of detecting sounds, such as voice activation/commands or other voice actions from the user, and may be integrated with or external to the wearable smart device 100. The speaker 132 may be one or more speakers or other devices capable of producing sounds and/or vibrations. The vibration unit 133 may be one or more vibration motors or actuators capable of providing haptic and tactile output. In certain implementations, the vibration unit 133 may also be capable of producing sounds, such that the speaker 132 and the vibration unit 133 may be the same or integrated.

The input device 134 may be an input device such as a touch sensor, a plurality of buttons or the like. In various embodiments, the microphone 131 may be considered an input device, such that the term "input device" may refer to the microphone, a button or buttons, a touchpad, a touchscreen or the like.

The display 135 may be a display integrated into the wearable smart device 100 or wirelessly connected to the wearable smart device 100 and may include an LCD screen, a touchscreen, one or more LED's or the like. The display 135 may be capable of displaying visual data from the stereo cameras 121 and/or the camera 122 as well as other data.

The component array 140 includes a battery 141, an antenna 142 and an input/output port (I/O port) 143. The battery 141 may be a battery or other power supply capable of powering the wearable smart device 100. The antenna 142 may be one or more antennas capable of transmitting and receiving wireless communications. For example, the antenna 142 may be a Bluetooth or WiFi antenna, a radio frequency identification (RFID) antenna or reader and/or a near field communication (NFC) unit. The I/O port 143 may be one or more ports for connecting additional peripherals. For example, the I/O port 143 may be a headphone jack, a data port or the like. The I/O port 143 may also be used in conjunction with the antenna 142 to communicate with remote devices.

The wearable smart device 100 includes one or more features allowing the wearable smart device 100 to be worn by a user. In some embodiments, the wearable smart device 100 may be implemented as a necklace, an earpiece, eyeglasses, a smart watch, a smart clip or the like. The necklace may drape over a user's neck and/or shoulders, eyeglasses may rest on a user's nose and/or ears, the smart watch may be worn around a user's neck or wrist, the smart clip may be clipped onto the user or an article of clothing of the user, etc.

Figure 2:
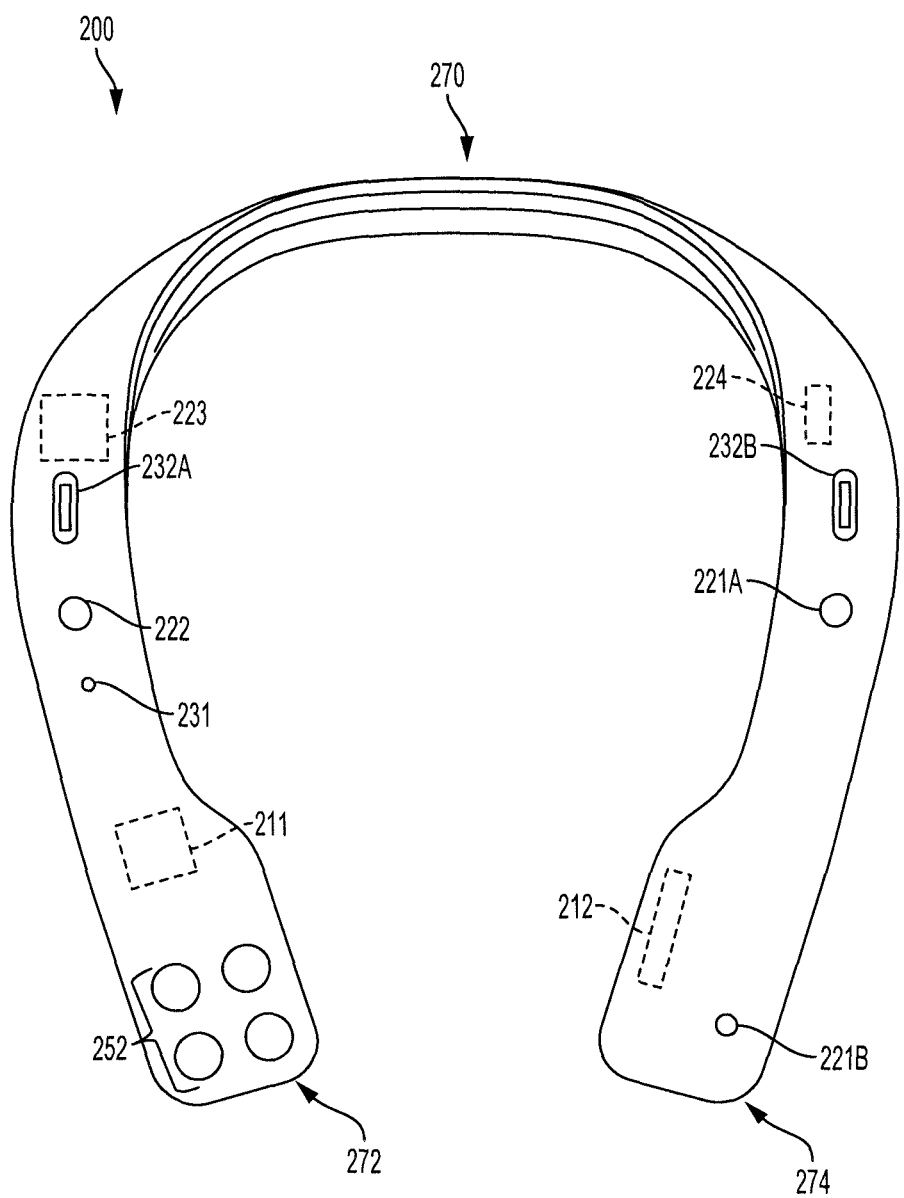
FIG. 2 illustrates a smart necklace as an example of the wearable smart device of FIG. 1 according to an embodiment of the present invention.

With reference now to FIG. 2, a wearable smart device may be embodied by a smart necklace 200. The smart necklace 200 has a top portion 270, a first end 272 and a second end 274. The smart necklace 200 is designed to be worn around a user's neck. In this regard, the top portion 270 is designed to rest against the back of a user's neck. While the top portion 270 is resting against the user's neck, the smart necklace 200 drapes over the user's shoulders such that the first end 272 and the second end 274 may be positioned on the front of the user's shoulders or the user's chest.

The smart necklace 200 includes a processor 211 and a memory 212. The processor 211 is configured to determine a navigational path and/or determine objects in the path of the user and to provide instructions to the user based on the navigation path or the objects. In this regard, the smart necklace 200 includes a camera 222, a stereo camera 221A, a stereo camera 221B, a GPS 124, an IMU 123 and a microphone 231. Data detected by these components may be used by the processor to detect a current location of the smart necklace 200 and/or to detect data in the environment surrounding the smart necklace 200. For example, the camera 222 and the stereo cameras 221A and 221B are configured to detect image data and provide the image data to the processor 211. The processor 211 may then determine if any navigational changes are upcoming such as a turn or object, an object, whether the user should change speed, direction or the like and determine when to provide the instructions to the user.

The smart necklace 200 includes an output unit 232A and an output unit 232B. The output unit 232A and the output unit 232B are each configured to generate output data that can be detected by a user of the smart necklace 200. In some embodiments, the output unit 232A and the output unit 232B may output one or more of audio data and haptic data. The output data may include navigation instructions and/or instructions for object avoidance.

The smart necklace 200 also includes buttons 252. The buttons 252 and/or the microphone 231 may be used as input devices to the smart necklace 200. For example, the user may be able to switch operating modes of the smart necklace 200 by selecting one or more of the buttons 252 or speaking an instruction that is detected by the microphone 231. The modes may include, for example, a navigation mode, an object avoidance mode, a find mode for finding particular objects or the like.

The smart necklace 200 is capable of providing navigation instructions to a selected destination, notifying the user of an upcoming object in the user's path and/or navigating the user around the object. In some embodiments, the smart necklace 200 may be used by individuals having one or more disabilities. For example, a blind person may wear and receive navigation instructions from the smart necklace 200. When discussed herein, a "turn" can refer to any change in current motion such as an actual turn, a change in movement to avoid an object, a change in speed or direction or the like.

The processor 211 is adapted to provide the navigation instructions at an ideal time so the blind individuals know exactly when to act. In order to determine the ideal time to alert a user of a turn or object, the processor 211 may first determine a speed of the user. The processor may determine the speed of the user based on data detected by at least one of the camera 222, the stereo cameras 221, the IMU 223 and/or the GPS 224. A speed determination based on one or more of image data and IMU data may be more accurate than other speed determinations. This is because the image data and IMU data can be detected in real time and are both highly accurate. On the other hand, speed determinations based on, for example, solely GPS data are less accurate.

In order to determine the time for providing the alert to the user, the processor 211 may also determine a distance to the turn or object. This may be determined using data detected by one or more of the GPS 224, the IMU 223, the camera 222 and/or the stereo cameras 221. The memory 212 may include map data such that a current location of the smart necklace 200 and a location of a turn or object are positioned on the map. Accordingly, the processor 211 may determine the distance to the turn or object based on the map data. In some embodiments, the processor 211 may determine the distance to a turn or object or an object using data detected by the camera 222 and/or the stereo cameras 221A and 221B. In some embodiments, the smart necklace 200 may include a Wi-Fi antenna such that the processor 211 can position the smart necklace 200 on the map based on a Wi-Fi positioning system.

When determining the timing for providing the alert to the user, the processor 211 may determine that the user should be alerted when the user is a particular distance away from the turn or object and/or when the user is a particular amount of time from the turn or object. The two can be used interchangeably because when a speed is known, a distance can be converted to an amount of time and vice versa. The ideal time for alerting the user to the upcoming turn or object may also be based on a learned response time of the user. For example, the processor 211 may learn that it takes the user a certain amount of time to respond to an alert based on data detected during prior navigations.

The ideal time for alerting the user may also be based on a current speed and/or an average speed of the user. In that regard, the processor 211 may also determine an average walking speed of a user for one or more categories as people may have different walking speeds when in different situations and environments. For example, a person may have one walking speed when walking indoors and another walking speed when walking outdoors, some people may have one walking speed when in a familiar place and another walking speed when in an unfamiliar place, some people may walk quicker on a hard surface than on a soft surface, etc.

Figure 3:
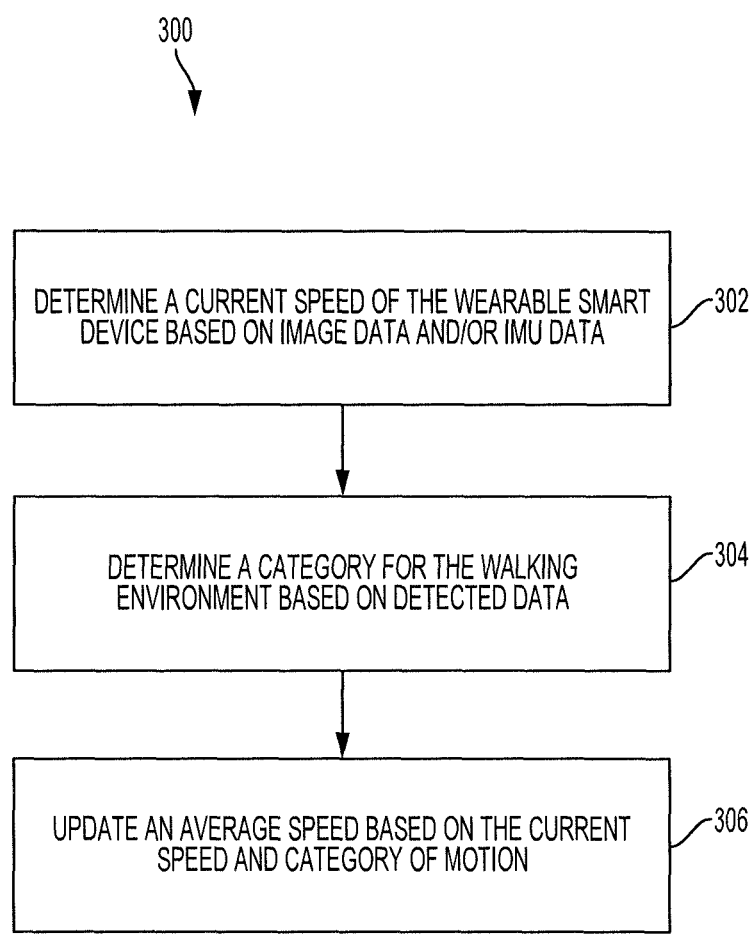
FIG. 3 illustrates a method for updating average speeds of a user based on detected walking environments according to an embodiment of the present invention.

With reference now to FIG. 3, a method 300 may be used by a processor such as the processor 211 of the smart necklace 200 for determining average speeds of a user. In some embodiments, the method 300 may be used by any wearable smart device or other device that provides navigation instructions.

In block 302, the processor may determine a current speed of the wearable smart device. The current speed may be detected based on various data such as map data, image data, IMU data or the like. In some embodiments, the processor may determine a current speed by detecting a distance to an object based on image data at a first point in time, detecting a new distance to the object based on image data at a second point in time and define the current speed as the change in distance divided by the change in time. In some embodiments, the processor may locate a current position of the wearable smart device on a map using one or more of image data and/or IMU data at a first point in time and locate a new current position of the wearable smart device on the map using one or more of image data and/or IMU data at a second point in time. The processor may then define the speed as the change in distance over the change in time. In some embodiments, the processor may determine a current speed by converting acceleration, rotational forces, magnetic forces and/or the like of the IMU into a speed measurement.

In block 304, the processor may determine a category for the walking environment of the user based on the detected data. The walking environment refers to characteristics of the user's environment that may affect a walking speed of the user. The categories may such factors as indoors versus outdoors, a crowded area versus a non-crowded area, whether the surface is slick, soft or neither or the like. The processor can determine a current walking environment based on data detected by one or more sensors. For example, image data and/or map data may indicate features such as how crowded an area is, whether the user is outdoors or indoors, whether a surface below the wearable smart device is soft or hard, and the like.

In block 306, the processor may update an average speed for the category of the walking environment based on the current speed. For example, the processor will update an average indoor speed when the user is walking indoors. In some embodiments, the wearable smart device may only record a single average speed.

Figure 4:
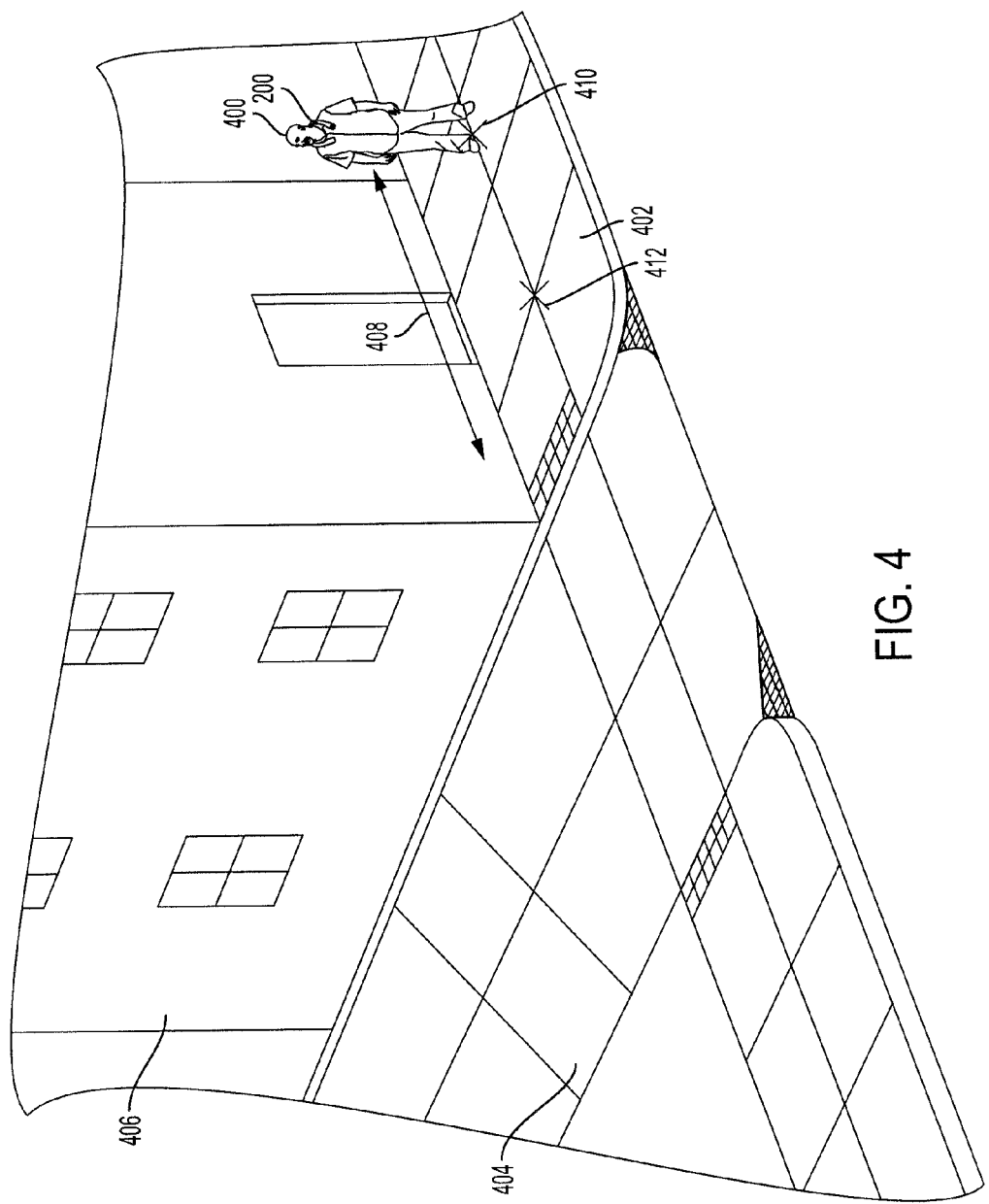
FIG. 4 illustrates an exemplary use of the method illustrated in FIG. 3 according to an embodiment of the present invention.

With reference now to FIG. 4, an exemplary use of the method 300 will be illustrated. In FIG. 4, a user 400 of the smart necklace 200 is walking along a sidewalk 402 that intersects with another sidewalk 404. At the intersection of the sidewalk 402 and the sidewalk 404 is a building 406. The smart necklace 200 may determine a walking speed of the user based on map data, image data, IMU data or the like. In some embodiments, the processor 211 may receive image data and measure a distance 408 between the user 400 and the end of the building 406 based on the image data. The processor 211 may continuously or periodically measure the distance 408 by, for example, using data detected by the stereo cameras 221 that indicate distance information. The processor 211 may then calculate a walking speed to be equal to the decrease of the distance 408 over a measured period of time. In various embodiments, the processor 211 may determine a first location 410 of the smart necklace 200 based on image data and/or IMU data, determine a second location 412 of the smart necklace 200 based on newly detected image data and/or IMU data and calculate the speed as the distance traversed over the amount of time to cover the distance.

Once the speed is determined, the processor 211 may determine a category for the walking environment of the smart necklace 200. Image data detected by the camera 222 and/or the stereo cameras 221A and 221B may indicate that the user 400 is currently outside based on, for example, a determination that the user 400 is on a sidewalk, that the user is seeing the outside of the building 406, an ambient brightness or the like. Additionally, the image data may indicate that the area is not crowded based on no other people or objects being detected. The image data may also indicate that the surface of the sidewalk 402 is hard and non-slippery. Accordingly, the processor 211 may determine that the category is characterized by the user being outside, on a hard surface and in a non-crowded location.

The processor 211 may then update the average speed of this category in the memory 212 based on the current speed. The average speed for each category may be any type of average including a running average, a weighted average, an average over time, an average over distance or the like.

Figure 5:
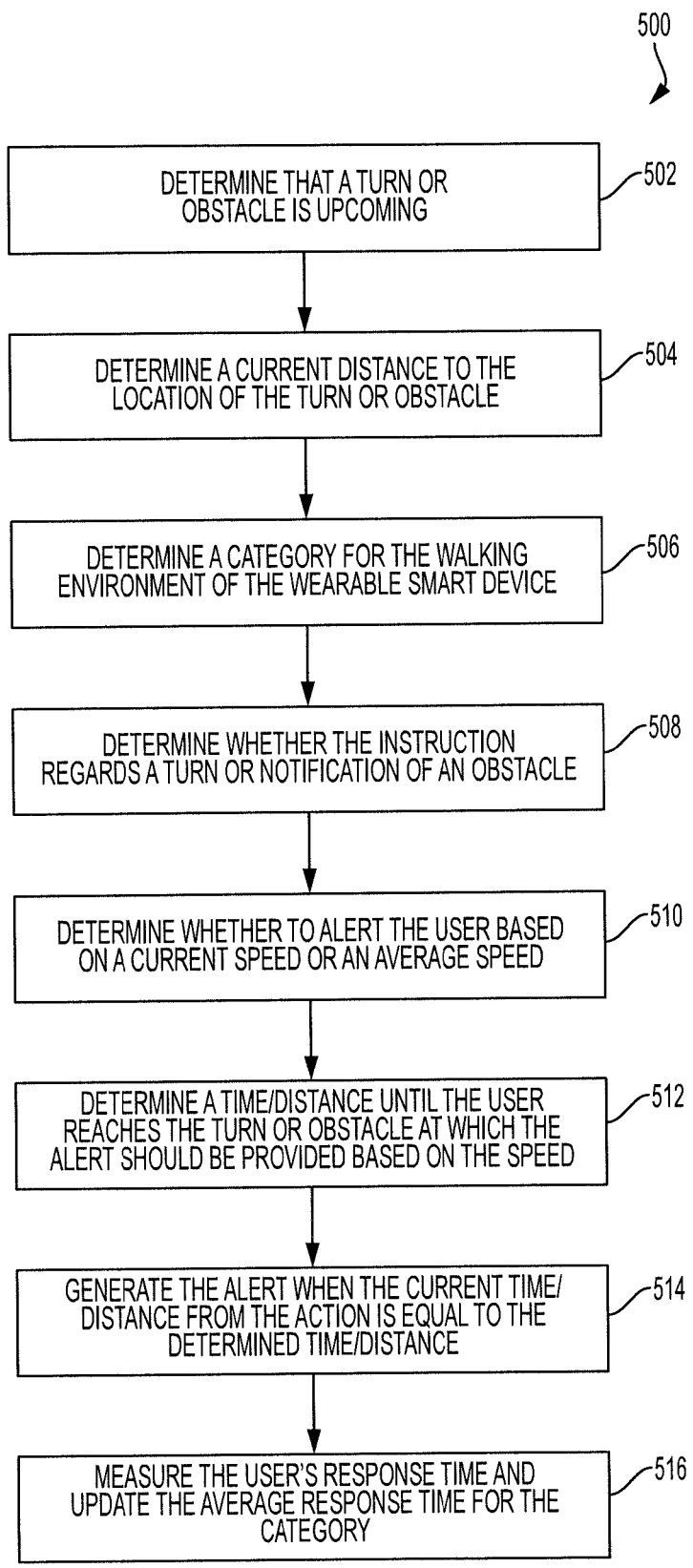
FIG. 5 illustrates a method for generating navigation instructions at an optimal time based on a user and the user's environment according to an embodiment of the present invention.

With reference now to FIG. 5, a method 500 may be used by a processor, such as the processor 111 or the processor 211, for alerting a user of an upcoming turn or object. The method 500 begins in block 502 in which the processor determines that the user is approaching a turn or object. In some embodiments, the processor may be operating in a navigation mode such that it may determine that a turn or object is upcoming based on a current location of the wearable smart device and map data. In some embodiments, the processor 211 may determine that an object, such as a ladder, a car or a crowd of people, is in the path of the user based on detected data such as image data. For example, the processor may determine, based on image data, that the user is walking towards a crowd at a rate that is faster than the crowd and that the user should slow down to avoid a collision.

In block 504, the processor may determine a current distance to the location of the turn or object. As described above, the wearable smart device may determine the distance to the location based on a current location and map data, image data or the like.

In block 506, the wearable smart device may determine a category for the walking environment of the user. This determination may be made in a similar manner as described above with reference to block 304 of FIG. 3.

In block 508, the processor may determine whether the instruction regards a turn or object. In some embodiments, the timing/distance at which the alert will be provided may vary based on whether the instruction is to turn or to avoid an object. For example, it is desirable for the user to turn at the precise moment when arriving at a turn but desirable for the user to turn prior to arriving at an object in the user's path. When the processor is alerting the user to the presence of an object, the processor may provide a warning at an earlier time/longer distance than if the processor is providing navigation instructions.

In block 510, the processor may determine whether to alert the user using a current speed or an average speed. In some embodiments, if the user is not currently moving or the type of terrain changes between the current location and the turn or object then it may be preferable to alert the user based on the average speed of the user on the final type of terrain. This is because the user may change speed on the final type of terrain or the speed may not be currently known. For example, if the user is walking on a sidewalk but the sidewalk changes to a rocky path then the user may slow down when he reaches the rocky path. Accordingly, it would be preferable to alert the user based on the user's average speed than current speed. Similarly, if the user's speed is erratic, it may be preferable to alert the user based on an average speed. However, if the terrain does not change and the user is holding a steady speed, it may be preferable to alert the user based on a current speed.

In block 512, the processor may determine a time or a distance (as discussed above, these can be used interchangeably) until the user reaches the turn or object at which the alert should be provided based on the current speed or the average speed. The time until the user reaches the turn or object may be determined based on the current speed and/or the average speed, a response time of the user, a length of the instruction, whether the instruction regards a turn or an object, any hazards presented by the turn or object and/or the like.

As described above, the processor may record an average response time of the user. The processor may also be capable of determining the length of any provided instruction.

The processor may determine any danger associated with a turn or object based on detected data as well. For example, map data or image data may indicate that a user should make a right turn on a sidewalk and that if the user walks past the sidewalk, he will walk directly into moving traffic. This represents a high level of danger to the user so the processor may determine to provide the instruction to turn at an earlier time than it would if no danger were present. This increases the likelihood that the user will in fact turn in a timely fashion and avoid walking into the moving traffic.

In some embodiments, the processor may determine a desirable walking speed in addition to alerting the user. For example, if the user should make a first turn that is immediately followed by a second turn, the processor may determine to instruct the user to walk slowly after the first turn so he/she doesn't miss the second turn. In some embodiments, the processor may inform the user of the first and second turn prior to the user reaching the first turn, again increasing the likelihood that the user will correctly make the second turn in time.

As an example of block 512, the user may be walking at 0.5 meters per second, may have an average response time of 1 second and an instruction for an upcoming turn or object may take 1 second to output. Accordingly, the processor may determine to output the instruction to turn or object 2 seconds prior to the user reaching the location of the turn or object.

Continuing the example, now the notification is regarding an object instead of a turn. If the instruction is provided 2 seconds prior to the user reaching the object, there is not much room for error if the user delays in reacting to the instruction. Accordingly, the processor may determine to add a predetermined amount of time when alerting the user to an object. In this example, the processor may alert the user 4 seconds prior to reaching the object—the two seconds for the response time and the output time and two additional seconds for safety purposes.

In order to determine when to output the navigation instruction, the processor may determine the distance to the turn or object at which the instruction should be output based on the timing and the current or average speed. For example, if the warning is to be generated 2 seconds prior to the user reaching the turn or object and the user is walking at a speed of 0.5 feet per second, then the alert should be generated when the distance from the user to the turn or object is approximately 1 foot.

In block 514, the processor may cause the instruction to be output when the distance from the location of the turn or object is equal to the distance determined in block 514. The processor may continuously or periodically calculate the current distance from the turn or object in order to generate the instruction at the proper time.

In block 516, the processor may measure the response time of the user and update the average response time for the particular category of movement. The response time may be measured by determining when the user has turned based on image data and/or IMU data and determine the time from when the instruction was output until the user has turned. In some embodiments, the memory may include only one response time average value instead of various response time average values that each correspond to a category of movement.

With reference now to FIG. 6, a database 600 associates speed information with various walking environment categories 602. The database 600 may be stored in a memory of a wearable smart device and accessible by a processor using a method similar to the method 500. Each of the walking environment categories 602 may correspond to an indoor class of categories and an outdoor class of categories and may each be distinguished based on various characteristics. For each of the walking environment categories 602, an average speed 604, a maximum speed 606, a minimum speed 608 and/or an average response time 610 may be stored in the database 600.

The average speed 604 corresponds to an average speed of the user for each particular walking environment category. The average speed 604 may be updated based on detected speeds while the user is in the particular walking environment category. In some embodiments, the wearable smart device may define additional walking environment categories over time. For example, the wearable smart device may determine that the user changes speeds in certain circumstances and may create a new category based on the certain circumstances.

The maximum speed 606 may correspond to a speed at which the processor will generate an alert to the user instructing the user to slow down. For example, in some walking environment categories such as the outdoor "crowded area-crowd still" walking environment category, it may be dangerous for the user to walk above a predetermined speed, such as 2.8 miles per hour. If a user is in this category and begins to walk at 2.8 miles per hour or faster, the wearable smart device may output an alert indicating that the user may be moving too fast for the particular walking environment category and should slow down.

Similarly, the minimum speed 608 may be a speed at which the processor will generate an alert if the user walks at or below that speed. For example, in the outdoor "crowded area-crowd moving" category, it may be dangerous for a user to walk slower than a predetermined speed, such as 1.8 miles per hour, as someone in the crowd may walk into the user. Accordingly, the wearable smart device may generate an alert if the user starts to move at 1.8 miles per hour or slower in a crowded area with the crowd moving.

The maximum speed 606 and the minimum speed 608 may be set values such that they do not change or may be variable values and change based on factors. For example, these values may change based on a speed of a crowd, a density of a crowd, an average walking speed of the user, how well a user maneuvers in particular environments or the like.

The average response time is the average time that it takes a user to respond to an alert while in each of the walking environment categories 602. As an example, in the indoor "obstructions in path" walking environment category, the user may perform a requested action one second after being provided the instruction. Continuing the example, if the user is walking through a mall with many kiosks (indoor "obstructions in path" walking environment category) and the processor determines that the user should turn ahead, the processor may determine to generate the instruction one second before the user is to turn to avoid the obstruction. Furthering the example, in some embodiments, the processor may take into consideration the time for the instruction to be provided. In these embodiments, if it takes the wearable smart device 2 seconds to output the instruction, the wearable smart device will begin to output the instruction 3 seconds prior to the user approaching the turn or object.

Figure 7:
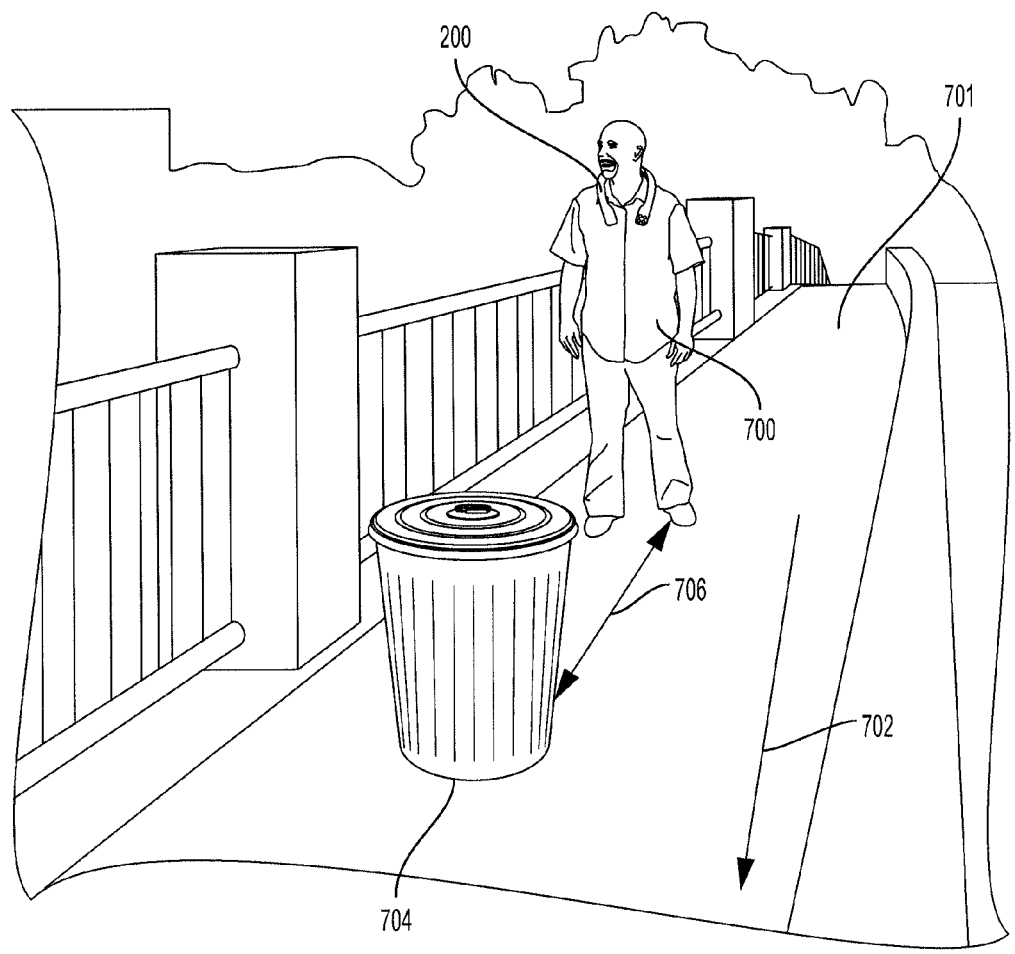
FIG. 7 illustrates an exemplary use of the method illustrated in FIG. 5 according to an embodiment of the present invention.

With reference now to FIG. 7, an exemplary use of the method 500 by the smart necklace 200 is illustrated. A user 700 is walking down a sidewalk 701 in the direction of an arrow 702. Directly in front of the user 700 is a trash can 704. The trash can 704 is a distance 706 from the user 700.

Cameras of the smart necklace 200 may detect the trash can 704 and determine that instructions should be provided to the user 700 to avoid the trash can 704. The processor 211 may also determine the distance 706 between the user 700 and the trash can 704. The processor 211 may determine that a walking environment category is the outdoor general category as it is not crowded, it is a hard surface, no obstructions are present in the path and the like. The processor 211 may further determine that the user should be alerted to the trash can 704 based on an average speed of the user 700 instead of a current speed or a distance.

The processor may determine that the user typically responds to alerts within 0.9 seconds after receiving them. The processor 211 may also determine that instructions for maneuvering around the trash can 704 will take 1.2 seconds to output. Accordingly, the processor 211 may determine that the smart necklace 200 should begin to output trash can avoidance instructions 2.1 seconds before the user 700 reaches the trash can 704 based on an average speed of 3.1 miles per hour. After providing the instructions to the user, the processor 211 may measure the response time of the user and update the average response time in the memory based on the measured response time.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for providing a user with navigation instructions comprising:
 a wearable smart device configured to be worn by the user and having:
  a camera configured to detect image data;
  an output unit configured to output one or more instructions that notify the user; and
  a processor coupled to the camera and the output unit, the processor configured to:
   determine a current speed of the wearable smart device based on the image data,
   cause, when an instruction relates to a first upcoming turn, the output unit to output the instruction to notify the user of the first upcoming turn at an amount of time or distance prior to reaching the first upcoming turn based on the current speed; and
   cause, when the instruction relates to a first upcoming object, the output unit to output the instruction to notify the user of the first upcoming object at an amount of time or distance prior to reaching the first upcoming object that is different than the amount of time or distance prior to reaching the first upcoming turn and based on the current speed.

2. The system of claim 1, wherein the wearable smart device has an inertial measurement unit (IMU) configured to detect inertial measurement data and wherein the processor is further configured to determine the current speed of the wearable smart device based on the inertial measurement data.

3. The system of claim 1, wherein the processor is further configured to determine a current walking environment of the wearable smart device based on the image data.

4. The system of claim 3, wherein the wearable smart device has a memory configured to store a first average speed of the wearable smart device corresponding to a first walking environment and a second average speed of the wearable smart device corresponding to a second walking environment, and wherein the processor is further configured to update the first average speed based on the current speed when a current walking environment matches the first walking environment and to update the second average speed based on the current speed when the current walking environment matches the second walking environment.

5. The system of claim 3, wherein the wearable smart device has a memory configured to store an average speed of the wearable smart device, and wherein the processor is further configured to determine the amount of time or distance prior to reaching the upcoming turn to notify the user and the amount of time or distance prior to reaching the upcoming object to notify the user based on the average speed.

6. The system of claim 3, wherein the wearable smart device has a memory configured to store a maximum speed corresponding to the current walking environment and wherein the processor is further configured to instruct the output unit to output data indicating that the current speed should be reduced when the current speed is greater than the maximum speed.

7. The system of claim 1, wherein the processor is further configured to determine an average response time of the user and to determine the amount of time or distance prior to reaching the upcoming turn to notify the user and the amount of time or distance prior to reaching the upcoming object to notify the user based on the average response time of the user.

8. The system of claim 1, wherein the processor is further configured to determine that the first upcoming turn or the first upcoming object based on a current location of the wearable smart device and map data.

9. The system of claim 1, wherein the processor is further configured to determine a current distance from the first upcoming turn or the first upcoming object and to cause the output unit to output the instruction to notify the user of the first upcoming turn or the first upcoming object based on the current distance from the first upcoming turn or the first upcoming object.

10. The system of claim 1, wherein the processor is further configured to determine that the wearable smart device will approach a second upcoming turn or a second upcoming object within a predetermined amount of time of the first upcoming turn or the first upcoming object and to instruct the output unit to output data indicating that the current speed should be reduced based on the determination that the wearable smart device will approach the second upcoming turn or the second upcoming object within the predetermined amount of time.

11. The system of claim 1, wherein the amount of time or distance prior to reaching the upcoming object is greater than the amount of time or distance prior to reaching the upcoming turn.

\* \* \* \* \*